(12) United States Patent
Damgaard et al.

(10) Patent No.: US 12,295,988 B2
(45) Date of Patent: *May 13, 2025

(54) SEMAGLUTIDE IN MEDICAL THERAPY

(71) Applicant: Novo Nordisk A/S, Bagsvaerd (DK)

(72) Inventors: Lars Holm Damgaard, Herlev (DK); Soeren Oestergaard Hardt-Lindberg, Virum (DK); Thomas Hansen, Broenshoej (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/820,792

(22) Filed: Aug. 30, 2024

(65) Prior Publication Data

US 2024/0415935 A1 Dec. 19, 2024

Related U.S. Application Data

(63) Continuation of application No. 18/736,608, filed on Jun. 7, 2024, now abandoned, which is a continuation of application No. 16/844,552, filed on Apr. 9, 2020, now Pat. No. 12,029,779, which is a continuation of application No. PCT/EP2018/077654, filed on Oct. 10, 2018.

(30) Foreign Application Priority Data

Oct. 12, 2017 (EP) .................... 17196254

(51) Int. Cl.
*A61K 38/26* (2006.01)
*A61K 9/00* (2006.01)
*A61P 3/04* (2006.01)

(52) U.S. Cl.
CPC ................ *A61K 38/26* (2013.01); *A61P 3/04* (2018.01); *A61K 9/0019* (2013.01)

(58) Field of Classification Search
None
See application file for complete search history.

(56) References Cited

U.S. PATENT DOCUMENTS

| | | | |
|---|---|---|---|
| 6,268,343 B1 | 7/2001 | Knudsen et al. | |
| 7,799,344 B2 | 9/2010 | Oberg | |
| 8,114,833 B2 | 2/2012 | Pedersen et al. | |
| 8,129,343 B2 | 3/2012 | Lau et al. | |
| 8,536,122 B2 | 9/2013 | Lau et al. | |
| 8,748,376 B2 | 6/2014 | Ludvigsen et al. | |
| 8,846,618 B2 | 9/2014 | Flink et al. | |
| 9,764,003 B2 | 9/2017 | Jensen | |
| 10,000,542 B2 | 6/2018 | Kofoed et al. | |
| 10,004,808 B2 | 6/2018 | Fox et al. | |
| 10,813,918 B2 | 10/2020 | During | |
| 11,291,658 B2 | 4/2022 | During | |
| 12,029,779 B2 * | 7/2024 | Groenning | A61K 9/10 |
| 2007/0203058 A1 | 8/2007 | Lau et al. | |
| 2010/0047762 A1 | 2/2010 | Button et al. | |
| 2010/0292133 A1 | 11/2010 | Spetzler et al. | |
| 2011/0301080 A1 | 12/2011 | Bush et al. | |
| 2015/0232527 A1 | 8/2015 | Gong et al. | |
| 2016/0108102 A1 | 4/2016 | Lau et al. | |
| 2019/0231876 A1 | 8/2019 | Pedersen et al. | |

FOREIGN PATENT DOCUMENTS

| | | | |
|---|---|---|---|
| CN | 102229668 A | 11/2011 | |
| CN | 104519902 A | 4/2015 | |
| CN | 108129565 A | 6/2018 | |
| RU | 2409349 C2 | 1/2011 | |
| RU | 2413530 C2 | 3/2011 | |
| WO | 2005/027978 A2 | 3/2005 | |
| WO | 2005049061 A2 | 6/2005 | |
| WO | 2006097537 A2 | 9/2006 | |
| WO | 2010/092163 A2 | 8/2010 | |
| WO | 2011080103 A1 | 7/2011 | |
| WO | 2011138421 A1 | 11/2011 | |
| WO | 12016419 A1 | 2/2012 | |
| WO | 2012080471 A1 | 6/2012 | |
| WO | 2012088379 A2 | 6/2012 | |
| WO | 2012107476 A1 | 8/2012 | |
| WO | 12130136 A1 | 10/2012 | |
| WO | 2012136790 A1 | 10/2012 | |
| WO | 2012177929 A2 | 12/2012 | |
| WO | 2014005858 A1 | 1/2014 | |
| WO | WO-2014177683 A1 * | 11/2014 | ........... A61K 31/166 |
| WO | 2017112824 | 6/2017 | |

OTHER PUBLICATIONS

Ahmann et al., "Efficacy and Safety of Once-Weekly Semaglutide Versus Exenatide ER after 56 Weeks in Subjects with Type 2 Diabetes (Sustain 3)," Diabetes Research and Clinical Practice, 2016, vol. 120, p. S51.

Anonymous: "NCT02453711 on Jul. 26, 2017: ClinicalTrials.gov Archive," Retrieved from Internet: URL:https://clincialtrials.gov/archive/NCT02453711/2017_07_26, retrieved on Jan. 26, 2018.

Aroda et al., "Efficacy and Safety of Once-Weekly Semaglutide Versus Once-Daily Insulin Glargine in Insulin-Naive Subjects with Type 2 Diabetes (Sustain 4)," Diabetes Research and Clinical Practice, 2016, vol. 120, p. S51.

Blundell et al., "Effects of once-weekly Semaglutide on appetite, energy intake, control of eating, food preference and body weight in subjects with obesity," Diabetes Obes Metab, 2017, vol. 19, pp. 1242-1251.

Chow et al., "Efficacy and Safety of Once-Weekly Semaglutide Versus Sitagliptin as Add-On to Metformin and/or Thiazolidinediones in Subjects with T2D (Sustain 2)," Diabetes Research and Clinical Practice, 2016, vol. 120, p. S122.

(Continued)

*Primary Examiner* — Sergio Coffa

(74) *Attorney, Agent, or Firm* — Leon Y. Lum

(57) ABSTRACT

The present invention relates to semaglutide for use in weight management.

1 Claim, No Drawings

(56) References Cited

OTHER PUBLICATIONS

Davies et al., "Dose-dependent glucose lowering and body weight reductions with the novel oral formulation of semaglutide in patients with early type 2 diabetes," Abstract 149, Diabetologia, 2016, vol. 59, Suppl. 1, p. S77.
Davies et al., "Effect of oral semaglutide compared with placebo and subcutaneous semaglutide on glycemic control in patients with type 2 diabetes," JAMA, 2017, vol. 218, No. 15, pp. 1460-1470.
Lingvay et al., "Treatment with semaglutide provides superior body weight reduction vs comparators in subjects with type 2 diabetes across the Sustain 1-5 trials," Abstract 817, Diabetologia, 2017, vol. 60, Suppl. 1, p. S377.
Nauck et al., "The once-weekly human GLP-1 analogue semaglutide provides significant reductions in HbA1c and body weight in patients with type 2 diabetes," Abstract 2, Diabetologia, 2012, vol. 55, Suppl. 1, p. S7.
Tan et al., "Efficacy and safety of once-weekly semaglutide for the treatment of type 2 diabetes," Expert Opin Investig Drugs, 2017, vol. 26, No. 9, pp. 1083-1089.
Nauck et al. "A phase 2, randomized, dose-finding study of the novel once-weekly human GLP-1 analog, semaglutide, compared with placebo and open-label liraglutide in patients with type 2 diabetes." Diabetes care, Feb. 2016, vol. 39, No. 2, pp. 231-241.
O'Neil et al. "Efficacy and safety of semaglutide compared with liraglutide and placebo for weight loss in patients with obesity: a randomised, double-blind, placebo and active controlled, dose-ranging, phase 2 trial." The Lancet, Aug. 2018, vol. 392, No. 10148, pp. 637-649.
Madsbad S et al. An Overview of once-weekly glucagon-like peptide-1 receptor agonists available efficacy and safety data and perspectives for the future, Diabetes, Obesity and Metabolism Year 2011, vol. 13, No. 5, pp. 394-407.
Buse B. J. et al., Exenatide once weekly versus liraglutide once daily in patients with type 2 diabetes (Duration-6): a randomised, open-label study, Lancet, 2013, vol. 381, pp. 117-124.
Kim et al. "Effects of Once-Weekly Dosing of a Long-Acting Release Formulation of Exentide on Glucose Control and Body Weight in Subjects with Type 2 Diabetes." Diabetes care (2007) vol. 30 pp. 1487-1493.
Bydureon NDA 022200/S-008 Package Information pp. 1-179 (Feb. 2014).
Clinical Trial NCT00696657 entitled "A Randomized Controlled Clinical Trial in Type 2 Diabetes Comparing Semaglutide to Placebo and Liraglutide." pp. Mar. 1-5, 2015. Accessed Sep. 24, 2015 at clinicaltrials.gov/archive/NCT00696657/2011_03_25.
Lau et al. "Discovery of the Once-WEekly Glucagon-Like Peptide-1 (GLP-1) Analogue Semaglutide." J. Med. Chem. (2015) vol. 58 pp. 7370-7380.
Eperzan Assessment Report. Euro. Med. Agency. pp. 1-124 (2014) accessed Sep. 24, 2015 at URL ema.europa.ed/docs/en_GB/document_library/EPAR_-_Public_assessment_report/human/002735/WC500165119.pdf.
Trulicity Assessment Report. Euro. Med. Agency. pp. 1-172 (2014) accessed Sep. 24, 2015 at URL ema.europa.ed/docs/en_GB/document_library/EPAR_-_Public_assessment_report/human/002825/WC500179473.pdf.
Mizuta et al. "The Role for GLP-1 in Regulation of Body Weight." Progress in Medicine 2008 vol 28 No. 8 pp. 1909-1912.
CDC, "National Health and Nutrition Examination Survey: Healthy Weight, Overweight and Obesity among U.S. adults" 03-0260 pp. 1-2 (Jul. 2003), accessed May 10, 2016 at URL cdc.gov/nchs/data/nhanes/databriefs/adultweight.pdf.
Application No. EP12/186,781, filed Oct. 1, 2012.
Application No. EP12174535, filed Jul. 1, 2012.
U.S. Appl. No. 61/694,837, filed Aug. 30, 2012.
U.S. Appl. No. 61/708,162, filed Oct. 1, 2012.

Astrup et al., "Effects of liraglutide in the treatment of obesity: a randomised, double-blind, placebo-controlled study." Lancet, Nov. 2009, vol. 374, No. 9701, pp. 1606-1616.
Astrup et al., "Safety, tolerability and sustained weight loss over 2 years with the once-daily human GLP-1 analog, liraglutide." Int J Obes (Lond). Jun. 2012, vol. 36, No. 6, pp. 843-854.
Barnett et al., "Obesity and Diabetes", John Wiley & Sons, Mar. 12, 2009, pp. 87-101.
Cleland et al., Formulation and Delivery of Proteins and Peptides, vol. 567, Aug. 1994, Chapter 1, p. 5.
Clinical trial: NCT00422058 "The Effect of Liraglutide on Body Weight in Obese Subjects 1I Without Diabetes" Jan. 2007, 1 Page.
European Medicines Agency EPAR Assessment Report for Victoza, Liraglutide , 2009, p. 7 and p. 9.
Examination Division Exam Dec. 12, 2006.
Frokjaer et al.,"Pharmaceutical formulation development of peptides and proteins", Jan. 2003, Chapter 8, p. 147.
Full prosecution file of the opposed patent EP2866825B1 that can be found in European Patent register https://register.epo.org/applicationlng=en&tab=doclist&number=EP13737808&filter=ALL Accessed Jan. 25, 2021.
Gibson, M., "Pharmaceutical Preformulation and Formulation: A Practical Guide from Candidate Drug Selection in Commercial Dosage Form", Drugs and the Pharmaceutical Sciences, Informa Healthcare, 2009, vol. 199, p. 327.
History of Changes for Study NCT00696657, ClinicalTrials.gov archive, Mar. 3, 2011.
Novo Nordisk announcement Semaglutide 2.4mg for obesity 2020, "Novo Nordisk files for US FDA regulatory approval of once-weekly semaglutide 2.4 mg for weight management" Dec. 4, 2020.
Novo Nordisk Clinical trial report: NN8022-I 807 "Effect of Liraglutide on Body Weight in Obese Subjects Without Diabetes" Feb. 8, 2010 p. 34.
Torekov et al., "Obesity-an indication for GLP-1 treatment?" Obesity pathophysiology and GIP-1 treatment potential, Obes Rev, Aug. 2011, vol. 12, No. 8, pp. 593-601.
European Medicines Agency EPAR Ozempic, Semaglutide, Assessment Report, 2018 p. 11 and p. 21.
Protocol of clinical trial NCT00696657 entitled A Randomised Controlled Clinical Trial in Type 2 Diabetes Comparing Semaglutide to Placebo and Liraglutide: Sep. 22, 2011, ClinicalTrials.gov archive, pp. 1-5.
Yakushinyaku, "General Consideration for Clinical Evaluations of New Drugs", Jun. 29, 1992, pp. 1-12.
Kapitza et al., "Semaglutide, a Once-Weekly Human GLP-1 Analog, Does Not Reduce the Bioavailability of the Combined Oral Contraceptive, Ethinylestradiol/Levonorgestrel," J Clin Pharmacol., May 2015, vol. 55, No. 5, pp. 497-504.
Holst JJ., "The physiology of glucagon-like peptide 1," Physiol Rev, Oct. 2007, vol. 87, No. 4, pp. 1409-1439.
Lovshin et al., "Incretin-based therapies for type 2 diabetes mellitus", Nature Reviews Endocrinology, May 2009, vol. 5, pp. 262-269.
Baggio et al., "Biology of Incretins: GLP-1 and GIP," Gastroenterology, 2007, vol. 132, pp. 2131-2157.
Ahmann et al., "Efficacy and Safety of Once-Weekly Semaglutide Versus Exenatide ER in Subjects With Type 2 Diabetes (Sustain 3): A 56-Week, Open-Label, Randomized Clinical Trial", Diabetes Care, Dec. 2017, vol. 41, No. 2, pp. 258-266.
Aroda et al., "Efficacy and safety of once-weekly semaglutide versus once-daily insulin glargine as add-on to metformin (with or without sulfonylureas) in insulin-naive patients with type 2 diabetes (Sustain 4): a randomised, open-label, parallel-group, multicentre, multinational, phase 3a trial", Lancet Diabetes Endocrinology, Mar. 2017, vol. 5, No. 5, pp. 355-366.
Li Jun et al., "Peoples Medical Publishing House" Clinical pharmacology 4th Edition, Jun. 2008, pp. 31, 48-49.
Saxenda, Full Prescribing Information, Sep. 2016, 28 pages.
U.S. Appl. No. 62/541,260, filed Aug. 4, 2017, 98 pages.
Ahrén et al., "Efficacy and Safety of Once-Weekly Semaglutide Versus Once-Daily Sitagliptin as an Add-on to Metformin, Thiazolidinediones, or Both, in Patients with Type 2 Diabetes

(56) References Cited

OTHER PUBLICATIONS (Sustain 2): A 56-Week Double-Blind, Phase 3a, Randomised Trial", Lancet, Apr. 2017, vol. 5, pp. 341-354.
Bhansali et al., "Historical Overview of Incretin Based Therapies", Journal of Association of Physicians of India, Jun. 2010, vol. 58, pp. 10-14.
Carracher et al., "American Association of Diabetes Educators 2017", Journal of Diabetes, Aug. 2017, pp. 1054-1057.
Davies et al., "Efficacy of Liraglutide for Weight Loss Among Patients with Type 2 Diabetes the Scale Diabetes Randomized Clinical Trial", Journal of the American Medical Association, Aug. 2015, vol. 314, No. 7, pp. 687-699.
Drucker et al., "The Incretin System: Glucagon-Like Peptide-1 Receptor Agonists and Dipeptidyl Peptidase-4 Inhibitors in Type 2 Diabetes", Lancet, Nov. 2006, vol. 368, pp. 1696-1705.
Holst et al., "Glucagon-Like Peptide 1 and Inhibitors of Dipeptidyl Peptidase IV in the Treatment of Type 2 Diabetes Mellitus", Current Opinion in Pharmacology, Oct. 2004, vol. 4, pp. 589-596.
Jensen et al., "Absorption, Metabolism and Excretion of the GLP-1 Analogue Semaglutide in Humans and Nonclinical Species", European Journal of Pharmaceutical Sciences, Mar. 2017, vol. 104, pp. 31-41.
Kalra et al., "Glucagon-like Peptide-1 Receptor Agonists in the Treatment of Type 2 Diabetes: Past, Present, and Future", Indian Journal of Endocrinology & Metabolism, Mar.-Apr. 2016, vol. 20, No. 2, pp. 254-267.
Kapitza et al., "Safety, Tolerability, Pharmacokinetics (PK) / Pharmacodynamics (PD) of Single Escalating Doses of Semaglutide, A Unique Once Weekly GLP-1 Analogue, in Healthy Male Subjects", Diabetologia, 2012, vol. 55, pp. S341.
Lund et al., "Glucagon-Like Peptide-1 Receptor Agonists for the Treatment of Type 2 Diabetes: Differences and Similarities", European Journal of Internal Medicine, Mar. 2014, vol. 25, pp. 407-414.
Marso et al., "Semaglutide and Cardiovascular Outcomes in Patients with Type 2 Diabetes", The New England Journal of Medicine, 16 Sep. 2016, vol. 375, No. 19, pp. 1834-1844.
Monami et al., "Effects of Glucagon-Like Peptide-1 Receptor Agonists on Body Weight: A Meta-Analysis", Experimental Diabetes Research, 2012, pp. 1-8.
Nauck et al., "Incretin-Based Therapies", Diabetes Care, Nov. 2009, vol. 32, Supplement 2, pp. S223-S231.
NCT01272232, "Effect of Liraglutide on Body Weight in Overweight or Obese Subjects with Type 2 Diabetes: Scale™ —Diabetes", May 2011, 4 pages.
NCT03144271, "Dose Escalation Trial of Single Subcutaneous Doses of NNC 0113-0217 to Assess Safety, Tolerability, Pharmacokinetics and Pharmacodynamics in Healthy Male Subjects", May 2017, 9 pages.
NCT02461589, "Dose-finding of Semaglutide Administered Subcutaneously Once Daily Versus Placebo and Liraglutide in Subjects With Type 2 Diabetes", Oct. 2017, 11 pages.
Novo Nordisk 2016 Form 6-K, Feb. 9, 2017, 124 pages.
Novo Nordisk Press Release, "Novo Nordisk reports up to 13.8% weight loss in people with obesity receiving semaglutide in phase 2 trial", Jun. 23, 2017, 2 pages.
Novo Nordisk, "Investor Presentation—First 6 months of 2017", 2017, 110 pages.
Novo Nordisk R&D Pipeline, "Semaglutide", 2010, 3 pages.
Ozempic Label, Highlights of Prescribing Information, Nov. 2024.
Peterson et al., "Glucose Dysregulation and Response to Common Anti-diabetic Agents in the FATZO/Pco Mouse", PLOS One, Jun. 2017, pp. 1-19.
Pi-Sunyer et al., "A Randomized, Controlled Trial of 3.0 mg of Liraglutide in Weight Management", New England Journal of Medicine, Jul. 2015, vol. 373, No. 1, pp. 11-22.

Smith, "Summary Review for Regulatory Action—Saxenda ", Center for Drug Evaluation and Research, Nov. 2014, pp. 1-37.
Sorli et al., "Efficacy and Safety of Once-Weekly Semaglutide Monotherapy Versus Placebo in Patients with Type 2 Diabetes (Sustain 1): A Double-Blind, Randomised, Placebo-Controlled, Parallel-Group, Multinational, Multicentre Phase 3a Trial", Lancet, Apr. 2017, vol. 5, pp. 251-260.
Victoza Label, Highlights of Prescribing Information, Jan. 2010.
Vilsboll et al., "Liraglutide, a Long-Acting Human Glucagon-Like Peptide-1 Analog, Given as Monotherapy Significantly Improves Glycemic Control and Lowers Body Weight Without Risk of Hypoglycemia in Patients with Type 2 Diabetes.", Jun. 2007, Diabetes Care, vol. 30, No. 6, pp. 1608-1610.
Bode et al., "10-Fold Liraglutide Overdose Over 7 Months Resulted Only in Minor Side-Effects", Journal of Clinical Pharmacology, 2013, vol. 53, No. 7, pp. 785-786.
Davies et al., "Supplemental Online Content, Efficacy of Liraglutide for Weight Loss Among Patients with Type 2 Diabetes the Scale Diabetes Randomized Clinical Trial", Journal of the American Medical Association, 2015, pp. 1-15.
Drugs at FDA Adlyxin, retrieved on Nov. 5, 2024 from: https://www.accessdata.fda.gov/scripts/cder/daf/index.cfm?event=overview.process&varApplNo=208471, 2 pages.
Drugs at FDA Byduryeon, retrieved on Nov. 5, 2024 from: https://www.accessdata.fda.gov/scripts/cder/daf/index.cfm?event=overview.process&varApplNo=022200, 3 pages.
Drugs at FDA Ozempic, retrieved on Nov. 5, 2024 from: https://www.accessdata.fda.gov/scripts/cder/daf/index.cfm?event=overview.process&varApplNo=209637, 2 pages.
Drugs at FDA Saxenda, retrieved on Nov. 5, 2024 from: https://www.accessdata.fda.gov/scripts/cder/daf/index.cfm?event=overview.process&varApplNo=206321, 3 pages.
Drugs at FDA Tanzeum, retrieved on Nov. 5, 2024 from: https://www.accessdata.fda.gov/scripts/cder/daf/index.cfm?event=overview.process&varApplNo=125431, 2 pages.
Drugs at FDA Trulicity, retrieved on Nov. 5, 2024 from: https://www.accessdata.fda.gov/scripts/cder/daf/index.cfm?event=overview.process&varApplNo=125469, 3 pages.
Drugs at FDA Victoza, retrieved on Nov. 5, 2024 from: https://www.accessdata.fda.gov/scripts/cder/daf/index.cfm?event=overview.process&varApplNo=022341, 4 pages.
Elmehdawi et al., "An Accidental Liraglutide Overdose: Case Report", Libyan Journal of Medicine, 2014, vol. 9, p. 1.
Jimenez-Solem et al., "Dulaglutide, a Long-Acting GLP-1 Analog Fused with an Fc Antibody Fragment for the Potential Treatment of Type 2 Diabetes", Current Opinion in Molecular Therapeutics, 2010, vol. 12, No. 6, pp. 790-797.
Nakanishi et al., "Attempted Suicide with Liraglutide Overdose Did Not Induce Hypoglycemia", Diabetes Research & Clinical Practice, Nov. 2012, vol. 99, p. e3-e4.
Novo Nordisk, "Investor presentation First 9 months of 2016", 2016, 113 pages.
American Diabetes Association, "Standards of Medical Care in Diabetes", Diabetes Care, Jan. 2004, vol. 27, Supplement 1, pp. S15-S35.
American Diabetes Association, "Standards of Medical Care in Diabetes", Diabetes Care, Jan. 2010, vol. 33, Supplement 1, pp. S11-S61.
UK Prospective Diabetes Study (UKPDS) Group, "Effect of Intensive Blood-Glucose Control with Metformin on Complications in Overweight Patients with Type 2 Diabetes (UKPDS 34)", Lancet, Sep. 1998, vol. 352, pp. 854-865.
Victoza Label, Highlights of Prescribing Information, Aug. 2017.

\* cited by examiner

SEMAGLUTIDE IN MEDICAL THERAPY

CROSS-REFERENCE TO RELATED APPLICATIONS

This application is a continuation of U.S. application Ser. No. 18/736,608, filed Jun. 7, 2024, which is a continuation of U.S. application Ser. No. 16/844,552, filed Apr. 9, 2020 (Issued U.S. Pat. No. 12,029,779), which is a continuation of International Application PCT/EP2018/077654 (WO2019/072941), filed Oct. 10, 2018, which claims priority to European Patent Application 17196254.1, filed Oct. 12, 2017; the contents of which are incorporated herein by reference.

The present invention relates to semaglutide for use in medical therapy in the form of weight management including treatment of obesity.

BACKGROUND

Weight management, including treatment of obesity, remains a challenge for many. Recently approved medical therapies exist, including Saxenda® which is the GLP-1 receptor agonist (GLP-1 RA) liraglutide authorised for chronic weight management in persons who are suffering from obesity or overweight with at least one weight-related comorbid condition. The most frequent adverse events for GLP-1 RAs are gastrointestinal disorders, and in particular nausea. Improved medical therapies for weight management are still desired.

SUMMARY

In some embodiments the present invention relates to a method for weight management of a subject in need thereof, wherein said subject is administered semaglutide in an amount of 2.0-4.0 mg once weekly. In some embodiments the present invention relates to a method for weight management of a subject in need thereof, wherein said subject is administered semaglutide in an amount of 2.2-2.7 mg per week.

DESCRIPTION

The present inventors surprisingly found that it is possible to administer semaglutide at high dosages, for example 2.0-4.0 mg once weekly, while achieving improved weight loss due to an unexpected beneficial ratio between the effect of semaglutide on body weight reduction and the safety profile observed for semaglutide at these high dosages. The present inventors also surprisingly found that the effect of semaglutide on body weight reduction continued to improve also through the high dosages of 0.3 and even 0.4 mg once daily. The present inventors also surprisingly found that the increase in safety profile, including gastrointestinal adverse events, at these high dosages surprisingly was lower than the improvement in body weight reduction. This is shown in the experimental section, where the change in the number of reported gastrointestinal adverse events was lower than change in body weight reduction for the high dosages of 0.3 and 0.4 mg once daily. To our knowledge no publications exists which describe the relationship between body weight reduction and safety profile of a GLP-1 receptor agonist in a population of obese human subjects which do not suffer from type 2 diabetes other than that for liraglutide, also discussed herein.

The term "safety profile" as used herein refers to adverse effects of an administered drug or other substance and includes gastrointestinal adverse events, such as nausea. In some embodiments the term "increase in safety profile" as used herein refers to an increase in safety events, such as an increase in gastrointestinal adverse events. In some embodiments the methods of the present invention provide acceptable tolerability while improving the treatment, e.g. improved weight management in the form of increased body weight loss. In some embodiments the term "safety profile" as used herein refers to tolerability. The term "gastrointestinal adverse event" as used herein refers to symptoms of the system organ class gastrointestinal disorders as defined by the MedDRA classification (e.g. version 19.1). In some embodiments "gastrointestinal adverse event" as used herein refers to symptoms selected from the group consisting of nausea, vomiting, diarrhoea and constipation. In some embodiments "gastrointestinal adverse event" as used herein refers to nausea.

In some embodiments the present invention relates to a method for weight management of a subject in need thereof, wherein said subject is administered semaglutide in an amount of 2.0-4.0 mg once weekly. In some embodiments the present invention relates to a method for weight management of a subject in need thereof, wherein said subject is administered semaglutide in an amount of 2.2-2.7 mg per week.

In some embodiments the method of the present invention provides an improved body weight reduction which also is relatively greater than the increase in gastrointestinal adverse events (such as nausea), particularly at the high semaglutide dosages of 0.3-0.4 mg per day (such as 2.2-2.7 mg per week or 2.0-4.0 mg once weekly). In other words, in some embodiments the method of the present invention provides an improved ratio between body weight reduction and gastrointestinal adverse events.

In some embodiments the present invention relates to a method for treating type 2 diabetes in a subject in need thereof, wherein said subject is administered semaglutide in an amount of 2.0-4.0 mg once weekly. In some embodiments the present invention relates to a method for treating type 2 diabetes in a subject in need thereof, wherein said subject is administered semaglutide in an amount of 2.2-2.7 mg per week.

Semaglutide

The GLP-1 RA semaglutide may be prepared as described in WO2006/097537, Example 4. Semaglutide is also known as $N^{6.26}$-{18-[N-(17-carboxyheptadecanoyl)-L-γ-glutamyl]-10-oxo-3,6,12,15-tetraoxa-9,18-diazaoctadecanoyl}-[8-(2-amino-2-propanoic acid),34-L-arginine]human glucagon-like peptide 1(7-37), see WHO Drug Information Vol. 24, No. 1, 2010.

Administration

In some embodiments semaglutide is administered by injection. In some embodiments, semaglutide is administered subcutaneously, such as via subcutaneous injection.

In some embodiments the amount of semaglutide administered per week is 2.2-2.7 mg. In some embodiments the amount of semaglutide administered per week is selected from the group consisting of 2.2-2.7 mg, 2.2-2.6 mg, and 2.3-2.5 mg. In some embodiments the amount of semaglutide administered per week is selected from the group consisting of 2.2 mg, 2.3 mg, 2.4 mg, 2.5 mg, 2.6 mg, and 2.7 mg.

In some embodiments semaglutide is administered once daily or once weekly.

In some embodiments semaglutide is administered once daily in an amount selected from the group consisting of 0.32-0.37 mg, 0.32-0.36 mg, and 0.33-0.35 mg once daily. In some embodiments semaglutide is administered once daily in an amount selected from the group consisting of 0.32 mg, 0.33 mg, 0.34 mg, 0.35 mg, 0.36 mg, 0.37 mg, and 0.37 mg once daily.

In some embodiments semaglutide is administered once weekly in an amount selected from the group consisting of 2.0-10.0 mg once weekly. In some embodiments semaglutide is administered once weekly in an amount selected from the group consisting of 2.0-4.0 mg once weekly. In some embodiments semaglutide is administered once weekly in an amount selected from the group consisting of 2.1-3.8 mg, 2.2-3.6 mg, and 2.3-3.4 mg. In some embodiments semaglutide is administered once weekly in an amount selected from the group consisting of 2.4-3.2 mg, 2.2-3.0 mg, and 2.0-2.8 mg. In some embodiments semaglutide is administered once weekly in an amount selected from the group consisting of 2.4-3.0 mg, 2.2-2.9 mg, and 2.0-2.8 mg. In some embodiments semaglutide is administered once weekly in an amount selected from the group consisting of 2.4-2.7 mg, 2.2-2.6 mg, and 2.0-2.5 mg. In some embodiments semaglutide is administered once weekly in an amount selected from the group consisting of about 2.2 mg, about 2.3 mg, or about 2.4 mg. In some embodiments semaglutide is administered once weekly in an amount selected from the group consisting of about 2.5 mg, about 2.6 mg, and about 2.7 mg.

In some embodiments the drug substance administered according to the method of the present invention consists of semaglutide.

Indications

In some embodiments the present invention relates to a method for weight management. In some embodiments the weight management is chronic weight management. In some embodiments the said weight management is selected from the group consisting of: reducing body weight, treating and/or preventing obesity, treating and/or preventing overweight, and preventing weight gain. In some embodiments the present invention relates to a method for reducing body weight. In some embodiments the present invention relates to a method for treating and/or preventing obesity. In some embodiments the present invention relates to a method for treating and/or preventing overweight. In some embodiments the present invention relates to a method for preventing weight gain. The term "overweight" as used herein refers to the condition wherein the subject has a BMI of at least 27, such as at least 27 to less than 30, including any number in between. The term "obesity" as used herein refers to the condition wherein the subject has a BMI of at least 30, such as at least 30 to less than 35, at least 35 to less than 40, or at least 40, including any number in between 30 and 40. The term "BMI" as used herein refers to the weight of a subject in kilograms divided by the square of the height of this subject in meters; BMI has the unit of $kg/m^2$.

In some embodiments the method of the invention provides an improved weight loss due to an unexpected beneficial ratio between the effect of semaglutide on body weight reduction and on gastrointestinal adverse events, such as nausea. In some embodiments the method of the invention reduces gastrointestinal adverse events in said subject. In some embodiments the method of the invention reduces gastrointestinal adverse events in the form of nausea in said subject. In some embodiments the term "reduces gastrointestinal adverse events" as used herein refers to the occurrence of fewer gastrointestinal adverse events, e.g. in comparison to other dosages of semaglutide.

In some embodiments the subject of the method of the invention is human. In some embodiments the subject of the method of the invention is adult. In some embodiments the subject of the method of the invention is a child (e.g. 2-11 years of age). In some embodiments the subject of the method of the invention is an adolescent (e.g. 12 to less than 18 years of age, such as 12 to 16 years of age or 12 to less than 16 years of age). In some embodiments the subject of the method of the invention has type 2 diabetes. In some embodiments the subject treated according to the methods of the present invention is obese (e.g. BMI≥30 or as defined herein in relation to the term "obesity") or overweight (e.g. BMI≥27 and BMI<30 or as defined herein in relation to the term "overweight"). In some embodiments the subject in the methods of the present invention has at least one weight-related comorbid condition (such as hypertension, type 2 diabetes mellitus, or dyslipidemia). In some embodiments the subject of the method of the invention has sleep apnoea and/or urine incontinence. In some embodiments the subject in the methods of the present invention has at least one weight-related comorbid condition selected from the group consisting of hypertension, type 2 diabetes mellitus, dyslipidemia, sleep apnoea, and urine incontinence.

Pharmaceutical Compositions

In some embodiments semaglutide is administered in the form of a pharmaceutical composition further comprising one or more pharmaceutically acceptable excipients, for example selected from the group consisting of buffer, isotonic agent, and preservative. The terms "pharmaceutical composition" and "composition" are used interchangeably herein and refer to a pharmaceutical composition. In some embodiments the composition is in the form of a solution or a suspension, such as an aqueous solution. In some embodiments pH of said composition is in the range of 6.0-10.0, such as 6.5-9.0 or 7.0-8.0. In some embodiments pH of said composition is in the range of 7.1-7.8, such as 7.2-7.6 or 7.3-7.5. In some embodiments pH of said composition is about 7.4. In some embodiments the concentration of semaglutide in said composition is 0.01-50 mg/ml, such as 0.05-20 mg/ml or 0.1-10 mg/ml. In some embodiments the concentration of semaglutide in said composition is 0.01-5 mg/ml, such as 0.05-2 mg/ml. In some embodiments the composition comprises a buffer, such as phosphate buffer. In some embodiments the composition comprises an isotonic agent, such as propylene glycol. In some embodiments the composition comprises a preservative, such as phenol. In some embodiments the drug substance in the composition consists of semaglutide. In some embodiments semaglutide is administered in the form of an aqueous composition comprising 4.1 mg/ml semaglutide, phosphate buffer, propylene glycol, phenol as preservative, at pH 7.4. In some embodiments semaglutide is administered in the form of an aqueous composition comprising 4.1 mg/ml semaglutide, 1.42 mg/ml disodium hydrogen phosphate dihydrate, 14.0 mg/ml propylene glycol, 5.50 mg/ml phenol, at pH 7.4. In some embodiments the composition pH is adjusted using hydrochloric acid and/or sodium hydroxide.

In some embodiments the term "a" means "one or more". In some embodiments, specific values mentioned herein and given in relation to numbers or intervals may be understood as the specific value or as about the specific value. In some embodiments the term "about" refers to ±10% of the value referred to. In some embodiments, terms presented in singular form also include the plural situation.

Embodiments of the Invention

Non-limiting embodiments of the invention include:
1. A method for weight management of a subject in need thereof, wherein semaglutide in an amount of 2.0-4.0 mg once weekly is administered to said subject.
2. A method for weight management of a subject in need thereof, wherein semaglutide in an amount of 2.2-2.7 mg per week is administered to said subject.
3. The method according to any one of the preceding embodiments, wherein said method reduces gastrointestinal adverse events in said subject.
4. The method according to the preceding embodiment, wherein said method reduces gastrointestinal adverse events in the form of nausea in said subject.
5. The method according to any one of the preceding embodiments, wherein said weight management is chronic weight management.
6. The method according to any one of the preceding embodiments, wherein said weight management is selected from the group consisting of:
   a. reducing body weight,
   b. treating and/or preventing obesity,
   c. treating and/or preventing overweight, and
   d. preventing weight gain.
7. The method according to any one of the preceding embodiments, wherein said amount of semaglutide administered per week is selected from the group consisting of 2.2-2.7 mg, 2.2-2.6 mg, and 2.3-2.5 mg.
8. The method according to any one of the preceding embodiments, wherein said amount of semaglutide administered per week is selected from the group consisting of 2.2 mg, 2.3 mg, 2.4 mg, 2.5 mg, 2.6 mg, and 2.7 mg.
9. The method according to any one of the preceding embodiments, wherein said administration is once daily or once weekly.
10. The method according to any one of the preceding embodiments, wherein said semaglutide administered once daily in an amount selected from the group consisting of 0.32-0.37 mg, 0.32-0.36 mg, and 0.33-0.35 mg once daily.
11. The method according to any one of the preceding embodiments, wherein said semaglutide administered once daily in an amount selected from the group consisting of 0.32 mg, 0.33 mg, 0.34 mg, 0.35 mg, 0.36 mg, 0.37 mg, and 0.37 mg once daily.
12. The method according to any one of the preceding embodiments, wherein said semaglutide is administered once weekly in an amount selected from the group consisting of 2.1-3.8 mg, 2.2-3.6 mg, and 2.3-3.4 mg.
13. The method according to any one of the preceding embodiments, wherein said semaglutide is administered once weekly in an amount selected from the group consisting of 2.4-3.2 mg, 2.2-3.0 mg, and 2.0-2.8 mg.
14. The method according to any one of the preceding embodiments, wherein said semaglutide is administered once weekly in an amount selected from the group consisting of 2.4-3.0 mg, 2.2-2.9 mg, and 2.0-2.8 mg.
15. The method according to any one of the preceding embodiments, wherein said semaglutide is administered once weekly in an amount selected from the group consisting of 2.4-2.7 mg, 2.2-2.6 mg, and 2.0-2.5 mg.
16. The method according to any one of the preceding embodiments, wherein said semaglutide is administered once weekly in an amount selected from the group consisting of 2.2 mg, 2.3 mg, 2.4 mg, 2.5 mg, 2.6 mg, and 2.7 mg.
17. The method according to any one of the preceding embodiments, wherein said subject is obese (BMI≥30) or overweight (BMI≥27).
18. The method according to the preceding embodiment, wherein said subject has at least one weight-related comorbid condition (such as hypertension, type 2 diabetes mellitus, or dyslipidemia).
19. The method according to any one of the preceding embodiments, wherein said semaglutide is administered subcutaneously, such as via subcutaneous injection.
20. The method according to any one of the preceding embodiments, wherein semaglutide is administered in the form of a composition further comprising one or more pharmaceutically acceptable excipients.
21. The method according to any one of the preceding embodiments, wherein said composition is in the form of a solution or a suspension, such as an aqueous solution.
22. The method according to any one of the preceding embodiments, wherein the pH of said composition is in the range of 6.0-10.0, such as 6.5-9.0 or 7.0-8.0.
23. The method according to any one of the preceding embodiments, wherein the pH of said composition is about 7.4.
24. The method according to any one of the preceding embodiments, wherein said pharmaceutically acceptable excipients comprises one or more excipients selected from the group consisting of isotonic agent, buffer, and preservative.
25. The method according to any one of the preceding embodiments, wherein the concentration of semaglutide in said composition is 0.01-50 mg/ml, such as 0.05-20 mg/ml or 0.1-10 mg/ml.
26. The method according to any one of the preceding embodiments, wherein the concentration of semaglutide in said composition is 0.01-5 mg/ml, such as 0.05-2 mg/ml.
27. The method according to any one of the preceding embodiments, wherein the drug substance administered consists of semaglutide.
28. The method according to any one of the preceding embodiments, wherein said subject is human.
29. The method according to any one of the preceding embodiments, wherein said subject is adult, adolescent or a child.
30. The method according to any one of the preceding embodiments, wherein said subject has type 2 diabetes.

EXAMPLES

Example 1: Semaglutide in Obese Subjects

A clinical trial was carried out in order to assess and compare the dose-response of five doses of once-daily semaglutide versus once-daily liraglutide 3.0 mg and/or placebo in inducing and maintaining weight loss after 52 weeks in obese subjects without diabetes mellitus. This trial was designed as a 52-week, randomised, double-blind, placebo-controlled, sixteen-armed, parallel group, multi-centre, multinational trial comparing once-daily subcutaneous administration of semaglutide in five different doses (ranging from 0.05 mg/day to 0.4 mg/day) with placebo in obese subjects without diabetes mellitus. Liraglutide 3.0 mg/day was included as an active comparator. The trial was double-blinded between active and placebo treatment. To ensure a sufficiently large sample of men, no more than 70% of the trial population was allowed to be women and the randomisation was stratified according to sex. Subjects were randomised in a balanced manner (6:1 active:placebo).

The primary endpoint was relative change from baseline in body weight (%) at 52 weeks. Key secondary endpoints included proportion of subjects with weight loss of ≥5% or ≥10% of baseline body weight at 52 weeks as well as change in body weight from baseline to 52 weeks. Supportive secondary safety endpoints also included gastrointestinal (GI) adverse events (i.e. nausea, vomiting, diarrhoea and constipation). During each site visit the individual subject was asked via open questions if they had experienced any medical problems since the last visit. All medical problems either observed by the site staff or the subject was reported as an adverse event and evaluated for severity and causality by the investigator. For this trial the subjects had site visits every 2 weeks for the first 20 weeks of the trial and afterwards site visits was performed every 4 weeks.

The treatment arms were: (A) semaglutide at randomised target dose 0.05, 0.1, 0.2, 0.3, or 0.4 mg (for dose levels above 0.05 mg, dose escalation took place every fourth week); (B) semaglutide at randomised target dose 0.3 or 0.4 mg (starting dose 0.05 mg with dose escalation every second week); (C) liraglutide 3.0 mg (starting dose 0.6 mg with dose escalation every week); and (D) placebo (matching each of the active treatment arms); all administered via subcutaneous injection. Subjects in all treatment arms including placebo received nutritional counselling and a calorie-reduced diet by a dietician or equivalent qualified delegate as well as physical activity counselling by a qualified person on a monthly basis beginning at the randomisation visit. The trial population consisted of a total of 957 subjects were randomised. A total of 777 subjects (81.2%) completed 52 weeks of treatment; 180 (18.8%) discontinued treatment prematurely with no obvious dose-dependent trend. Key inclusion criteria for this trial were: Male or female, age≥18 years at the time of signing inform consent; body mass index (BMI)≥30.0 kg/m2 at the screening visit; and at least one unsuccessful weight loss attempt per investigator judgement. Key exclusion criteria for this trial were: A HbA1c≥6.5% at screening or diagnosed with type 1 or type 2 diabetes mellitus; Treatment with glucose lowering agent(s) within 90 days before screening; Screening calcitonin≥50 ng/L (pg/mL); Personal or family history of medullary thyroid carcinoma or multiple endocrine neoplasia syndrome type 2; History of pancreatitis (acute or chronic); Obesity induced by endocrine disorders (e.g. Cushing Syndrome); Treatment with any medication within 90 days before screening that based on investigator's judgement may cause significant weight change; Previous surgical treatment for obesity (liposuction and/or abdominoplasty performed >1 year before screening is allowed); History of major depressive disorder within 2 years before randomisation; Any lifetime history of a suicidal attempt; and Female who is pregnant, breast-feeding or intends to become pregnant or is of childbearing potential and not using an adequate contraceptive method (adequate contraceptive measures as required by local regulation or practice).

Statistical analyses of effect endpoints: The primary analysis was based on a 'jump-to-reference' multiple imputation approach (J2R-MI). Week 52 data from subjects who discontinued trial product and returned for the visit at week 52 were included in the analysis. First, an imputation model using observed week 52 body weight (kg) measurements from the placebo arm only were estimated. Second, multiple copies (1000) of the full analysis set were generated by imputing missing values in all treatment arms from the imputation model. The primary endpoint was calculated in each complete data set and analysed using an analysis of covariance (ANCOVA) model. Third, the 1000 analysis results were summarised using Rubin's formula. Pairwise treatment differences (95% confidence intervals [CIs]) between semaglutide and placebo, liraglutide 3.0 mg and placebo, different semaglutide doses, and semaglutide and liraglutide 3.0 mg at week 52 were provided from the analysis model. With this multiple imputation method it was assumed that; subjects in the placebo arm with missing endpoint data at week 52 had a response similar to the completers in the placebo arm and that subjects in the active treatment arms with missing endpoint data at week 52 were in the placebo arm during the entire trial regardless of the time of discontinuation.

Subject baseline characteristics for body weight and body mass index (BMI) are shown in Table 1. Results are shown in Tables 2-6 herein.

TABLE 1

Baseline characteristics of subjects per treatment arm, presented as mean (SD)

|  | N | Body weight (kg) | BMI (kg/m²) |
| --- | --- | --- | --- |
| Sema 0.5 mg | 103 | 111 (23.2) | 39.1 (6.5) |
| Sema 0.1 mg | 102 | 111 (21.5) | 39.6 (7.4) |
| Sema 0.2 mg | 103 | 114 (24.5) | 40.1 (7.0) |
| Sema 0.3 mg | 103 | 112 (23.0) | 39.6 (7.1) |
| Sema 0.4 mg | 102 | 113 (26.4) | 39.9 (8.8) |
| Lira 3.0 mg | 103 | 109 (21.9) | 38.6 (6.6) |
| Placebo Pool | 136 | 114 (25.4) | 40.1 (7.2) |

N: Number of subjects, Lira: Liraglutide, Sema: Semaglutide, SD: Standard deviation.

TABLE 2

Change in body weight (%) from baseline to week 52 by treatment arm - descriptive statistics - observed data - full analysis set

|  | Subjects on-treatment | | Subjects in-trial | |
| --- | --- | --- | --- | --- |
|  | N | Mean (SD) | N | Mean (SD) |
| Sema 0.5 mg | 77 | −6.79 (5.76) | 92 | −6.33 (6.26) |
| Sema 0.1 mg | 88 | −9.76 (7.97) | 96 | −9.11 (8.05) |
| Sema 0.2 mg | 87 | −13.68 (8.94) | 94 | −12.54 (9.64) |
| Sema 0.3 mg | 88 | −12.97 (8.22) | 95 | −12.06 (8.94) |
| Sema 0.4 mg | 82 | −16.17 (8.37) | 100 | −13.96 (9.30) |
| Lira 3.0 mg | 86 | −9.20 (6.66) | 96 | −8.26 (7.10) |
| Placebo Pool | 103 | −2.28 (5.67) | 123 | −2.33 (6.11) |

N: Number of subjects, SD: Standard deviation, Subjects on-treatment: Subjects who completed treatment through to trial end, Subjects in-trial: Subjects on-treatment as well as subjects who discontinued treatment prior to trial end but presented at the week 52 visit.

TABLE 3

Change in body weight (%) from baseline to week 52 by treatment arm and treatment differences - primary statistical analysis - ANCOVA - J2R-MI - full analysis set

| | Change (%) | | Treatment difference (%-points)* | |
|---|---|---|---|---|
| | N | Estimate | vs. Placebo Pool | vs. Lira 3.0 mg |
| Sema 0.05 mg | 92 | −5.99 | −3.70 [−5.91; −1.49] | 1.77 [−0.58; 4.12] |
| Sema 0.1 mg | 96 | −8.62 | −6.32 [−8.52; −4.13] | −0.85 [−3.19; 1.48] |
| Sema 0.2 mg | 94 | −11.60 | −9.31 [−11.51; −7.10] | −3.83 [−6.18; −1.49] |
| Sema 0.3 mg | 95 | −11.17 | −8.88 [−11.08; −6.68] | −3.41 [−5.75; −1.06] |
| Sema 0.4 mg | 100 | −13.84 | −11.55 [−13.74; −9.36] | −6.08 [−8.41; −3.75] |
| Lira 3.0 mg | 96 | −7.76 | −5.47 [−7.68; −3.27] | — |
| Placebo Pool | 123 | −2.29 | — | −5.47 [−7.68; −3.27] |

Sema: Semaglutide, Lira: Liraglutide, Placebo Pool: Placebo subjects in all treatment arms, *data shown as "Estimate [95% CI]", N: Number of subjects contributing to analysis, CI: Confidence interval. J2R-MI: Analysis of in-trial data with missing observations imputed from the pooled placebo arms based on a jump to reference multiple (×1000) imputation approach. Week 52 responses were analysed using an analysis of covariance model with treatment, region and sex as factors and baseline body weight as covariate. Treatment comparisons are not adjusted for multiple testing.

TABLE 4

Change in body weight (%) from baseline at week 52 - results from Emax dose-response modelling - ANCOVA - J2R-MI - full analysis set

| | Model prediction* (Estimate [95% CI]) | |
|---|---|---|
| | % | Corresponding Sema dose** |
| Sema 0.05 mg | −6.19 [−7.18; −5.21] | — |
| Sema 0.1 mg | −8.47 [−9.45; −7.49] | — |
| Sema 0.2 mg | −11.00 [−11.75; −10.25] | — |
| Sema 0.3 mg | −12.37 [−13.23; −11.52] | — |
| Sema 0.4 mg | −13.24 [−14.37; −12.10] | — |
| Lira 3.0 mg | — | 0.08 [0.06; 0.11] |

Lira: Liraglutide, Sema: Semaglutide, *The dose-response coefficients were estimated via an Emax three parameter model, **Based on %.

TABLE 5

Summary of gastrointestinal adverse events in subjects on-treatment observed data and results from Emax dose-response modelling - full analysis set

| | Observed data | | | Model prediction* (Estimate [95% CI]) | |
|---|---|---|---|---|---|
| | N | $N_e$ | % | % | Corresponding Sema dose** |
| Sema 0.05 mg | 103 | 64 | 62.1 | 61.8 [53.8; 69.8] | — |
| Sema 0.1 mg | 102 | 72 | 70.6 | 68.3 [63.1; 73.6] | — |
| Sema 0.2 mg | 103 | 72 | 69.9 | 73.2 [69.1; 77.2] | — |
| Sema 0.3 mg | 103 | 72 | 69.9 | 75.1 [70.2; 80.1] | — |
| Sema 0.4 mg | 102 | 84 | 82.4 | 76.2 [70.4; 82.0] | — |
| Lira 3.0 mg | 103 | 77 | 74.8 | — | 0.28 [−0.02; 0.57] |
| Placebo Pool | 136 | 52 | 38.2 | — | — |

Lira: Liraglutide, Sema: Semaglutide, N: Number of subjects, $N_e$: Number of subjects experiencing at least one event, %: Percentage of subjects with at least one event, *The dose-response coefficients were estimated via an Emax three parameter model, **Based on %.

TABLE 6

Summary of gastrointestinal adverse events in the form of nausea in subjects on-treatment - observed data - full analysis set

| | N | $N_e$ | % | E |
|---|---|---|---|---|
| Sema 0.05 mg | 103 | 32 | 31.1 | 41 |
| Sema 0.1 mg | 102 | 42 | 41.2 | 80 |
| Sema 0.2 mg | 103 | 45 | 43.7 | 74 |
| Sema 0.3 mg | 103 | 43 | 41.7 | 69 |

TABLE 6-continued

Summary of gastrointestinal adverse events in the form of nausea in subjects on-treatment - observed data - full analysis set

| | N | $N_e$ | % | E |
|---|---|---|---|---|
| Sema 0.4 mg | 102 | 49 | 48.0 | 94 |
| Lira 3.0 mg | 103 | 46 | 44.7 | 89 |
| Placebo Pool | 136 | 24 | 17.6 | 30 |

Lira: Liraglutide, Sema: Semaglutide, N: Number of subjects, $N_e$: Number of subjects experiencing at least one event, %: Percentage of subjects experiencing at least one event, E: Number of events Surprisingly, the results in Tables 2-4 show that the effect of semaglutide on body weight reduction continued to improve also through the high dosages of 0.3 and even 0.4 mg once daily. The results in Tables 5-6 show that the increase in gastrointestinal adverse events was relatively lower at these high dosages and, upon comparison to e.g. Table 4, these increases surprisingly were relatively lower than the improvement in body weight reduction. Specifically, the results in Tables 4-5 show that the dosage of semaglutide providing the same body weight reduction as 3.0 mg liraglutide is 0.08 mg semaglutide (with a 95% CI of [−0.02;0.57]) whereas the dosage of semaglutide providing the same level of gastrointestinal adverse events as 3.0 mg liraglutide is 0.28 mg semaglutide (with a 95% CI of [−0.02;0.57]); thus semaglutide provides around 3 times greater body weight reduction at the same level of gastrointestinal adverse events (the around 3 times was calculated as (3.0/0.08)/(3.0/0.28). Overall, these results show that a semaglutide product for weight management is possible to administer to at high dosages resulting in improved weight loss due to this unexpected good ratio between body weight reduction and gastrointestinal adverse events. Even more surprisingly, the ratio between body weight reduction and gastrointestinal adverse events is improved at the highest semaglutide dosages of 0.3 and even 0.4 mg once daily compared to the lower dosages.

Example 2: Semaglutide in Subjects With Type 2 Diabetes

A 26-week, randomized, double-blind clinical trial was carried out with adult patients with T2D, $HbA_{1c}$ 7.0-10.0% (53-86 mmol/mol), and body mass index 24.0-40.0 kg/m² who were treated with diet and exercise±metformin. Patients were randomized 2:2:1 to once-daily semaglutide, placebo or liraglutide in one of four volume-matched doses (semaglutide: 0.05, 0.1, 0.2, 0.3 mg; liraglutide: 0.3, 0.6, 1.2, 1.8 mg) by subcutaneous injection. The primary endpoint was change in $HbA_{1c}$ from baseline to week 26. Key exclusion criteria were a history of chronic or idiopathic acute pancreatitis and moderate-to-severe renal impairment (estimated glomerular filtration rate<60 mL/min/1.73 m$^2$).

Trial drug administration: Following a 2-week screening period, patients received trial medication for 26 weeks, followed by a 7-week follow-up period. Patients were initiated on treatment with 0.05 mg semaglutide, 0.3 mg liraglutide or 50 µL placebo, all administered subcutaneously once daily, and titrated every 4 weeks up to their final randomized dose. This titration algorithm was used in all patients to ensure blinding across the products, and thus liraglutide was escalated at a slower pace than recommended in the label. The trial was double blinded within (but not between) each dose level of semaglutide, liraglutide and placebo, as treatment was volume matched.

Subject baseline characteristics for body weight and body mass index (BMI) are shown in Table 7. Results for body weight change and gastrointestinal adverse events are shown in Table 8.

TABLE 7

Baseline characteristics of subjects per treatment arm, presented as mean (SD)

| | Sema 0.05 mg (n = 64) | Sema 0.1 mg (n = 63) | Sema 0.2 mg (n = 65) | Sema 0.3 mg (n = 63) | Lira 0.3 mg (n = 64) | Lira 0.6 mg (n = 64) | Lira 1.2 mg (n = 64) | Lira 1.8 mg (n = 65) | Pooled placebo (n = 129) |
|---|---|---|---|---|---|---|---|---|---|
| Body weight (kg) | 93.4 (18.3) | 92.4 (17.2) | 98.1 (17.9) | 94.8 (17.8) | 92.25 (17.5) | 92.7 (16.5) | 96.7 (18.3) | 93.4 (19.3) | 94.0 (17.8) |
| BMI (kg/m$^2$) | 32.3 (4.6) | 32.4 (4.5) | 32.8 (4.5) | 33.1 (4.7) | 32.9 (3.9) | 33.0 (4.3) | 33.3 (4.3) | 32.1 (4.5) | 32.8 (4.15) | n: Number of subjects, Lira: Liraglutide, Sema: Semaglutide, SD: Standard deviation

TABLE 8

Mean change in body weight and gastrointestinal adverse events, including nausea, from baseline to week 26-on-treatment-estimated data

| | Body weight change, | | Gastrointestinal adverse events | | | Nausea | | |
|---|---|---|---|---|---|---|---|---|
| | N | mean (kg) | N$_e$ | % | E | N$_e$ | % | E |
| Sema 0.05 mg | 64 | −2.8 | 21 | 32.8 | 61 | 11 | 17.2 | 16 |
| Sema 0.1 mg | 63 | −4.3 | 28 | 44.4 | 90 | 12 | 19.0 | 20 |
| Sema 0.2 mg | 65 | −6.7 | 30 | 46.2 | 106 | 14 | 21.5 | 22 |
| Sema 0.3 mg | 63 | −8.2 | 34 | 54.0 | 101 | 16 | 25.4 | 22 |
| Lira 0.3 mg | 64 | −1.5 | 14 | 21.9 | 25 | 6 | 9.4 | 7 |
| Lira 0.6 mg | 64 | −1.7 | 19 | 29.7 | 62 | 7 | 10.9 | 11 |
| Lira 1.2 mg | 64 | −1.7 | 20 | 31.3 | 40 | 7 | 10.9 | 11 |
| Lira 1.8 mg | 65 | −3.7 | 27 | 41.5 | 81 | 13 | 20.0 | 18 |
| Pooled placebo | 129 | −1.2 | 29 | 22.5 | 54 | 6 | 4.7 | 7 |

Lira: Liraglutide, Sema: Semaglutide, N: Number of subjects, N$_e$: number of patients experiencing at least one event, %: percentage of patients experiencing at least one event, E: number of events. The 'on-treatment' overview includes treatment-emergent adverse events with onset at or after the date of the first trial product dose and before or at the date of the last trial product dose plus 7 weeks plus the 7 days visit window for the end-of-treatment follow-up visit (=56 days). The observation time is the duration of this period.

Surprisingly, the results in Table 8 show that the effect of semaglutide on body weight reduction continued to improve also through the high dosage of 0.3 mg once daily and that the increase in gastrointestinal adverse events was relatively lower at this high dosage and surprisingly was relatively lower than the improvement in body weight reduction. Overall, these results therefore show that a semaglutide product for weight management is possible to administer to at high dosages resulting in improved weight loss due to this unexpected good ratio between body weight reduction and gastrointestinal adverse events. Even more surprisingly, the ratio between body weight reduction and gastrointestinal adverse events is improved at the highest semaglutide dosages of 0.3 mg once daily compared to the lower dosages.

TABLE 9

Change in HbA1c (Glycosylated Haemoglobin)

| | N | Mean Change in HbA1c % (SD) |
|---|---|---|
| Sema 0.05 mg | 64 | −0.97 (0.85) |
| Sema 0.1 mg | 63 | −1.30 (1.03) |
| Sema 0.2 mg | 65 | −1.65 (0.79) |
| Sema 0.3 mg | 63 | −1.96 (0.95) |
| Lira 0.3 mg | 64 | −0.50 (0.93) |
| Lira 0.6 mg | 64 | −0.88 (0.90) |
| Lira 1.2 mg | 64 | −0.86 (0.92) |
| Lira 1.8 mg | 65 | −1.32 (0.78) |
| Pooled placebo | 129 | −0.05 (0.90) |

Lira: Liraglutide, Sema: Semaglutide, N: Number of subjects, SD: Standard Deviation While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for treating type 2 diabetes in a subject in need thereof, comprising administering semaglutide to the subject in an amount of 2.0 mg once weekly, wherein the semaglutide is administered subcutaneously.

\* \* \* \* \*